| United States Patent [19] | [11] | 4,227,012 |
|---|---|---|
| Suld et al. | [45] | Oct. 7, 1980 |

[54] OXIDATION OF METHYL BENZENES IN THE PRESENCE OF ACETIC ACID AND A DEHYDRATING AGENT

[75] Inventors: George Suld, Springfield; James E. Lyons, Wallingford; Robert W. Shinn, Aston, all of Pa.

[73] Assignee: Suntech, Inc., Philadelphia, Pa.

[21] Appl. No.: 957,613

[22] Filed: Nov. 3, 1978

[51] Int. Cl.³ .......................................... C07C 69/035
[52] U.S. Cl. ................................ 560/131; 568/806; 560/263; 568/470
[58] Field of Search ........................................ 560/131

[56] References Cited

U.S. PATENT DOCUMENTS 3,772,383  11/1973  Kominami et al. ................. 560/131
4,056,572  11/1977  Bashkirov et al. .................. 560/131

OTHER PUBLICATIONS

Grozhan et al., Doklady Akad. Nauk. SSSR, 204 (4), 872-873 (1972).

*Primary Examiner*—Jane S. Myers
*Attorney, Agent, or Firm*—J. Edward Hess; Donald R. Johnson; Stanford M. Back

[57] ABSTRACT

Oxidation of methyl benzenes with air or oxygen to form a phenolic acetate and formaldehyde or methylene diacetate may be carried out in the presence of acetic acid, phosphorus pentoxide, benzaldehyde and an acid catalyst. The resulting acetates may then be pyrolyzed to yield phenolic compounds and formaldehyde, respectively.

9 Claims, No Drawings

OXIDATION OF METHYL BENZENES IN THE PRESENCE OF ACETIC ACID AND A DEHYDRATING AGENT

BACKGROUND OF THE INVENTION

This invention relates to a novel process for the oxidation of methyl benzenes. More particularly, this invention relates to an improved process for the oxidation of methyl benzenes with air or oxygen in the presence of acetic acid, $P_2O_5$, and sulfuric acid under mild conditions to form a phenolic acetate and formaldehyde or methylene diacetate. These compounds may then be converted to the corresponding phenolic compound and formaldehyde or paraformaldehyde by, for example, pyrolysis.

Earlier work of Grozhan et al, (Doklady Akad. Nauk, SSSR, 204, No. 4,872) established that acid catalyzed oxidation of toluene at high temperature and pressure in acetic anhydride followed by saponification of the reaction product gave phenol in modest yield. More recent work of Lyons, Suld and Shinn application Serial No. 945,747 has shown that phenyl acetate, methylene diacetate and acetic acid are the major products of the acid catalyzed air oxidation of toluene in acetic anhydride. This reaction is also characterized by relatively high temperatures and pressures. In copending application, Ser. No. 957,614, Suld et al. have demonstrated that when methyl benzenes are oxidized in acetic anhydride, but in the added presence of benzaldehyde, the reaction may be carried out at much milder temperatures and pressures then heretofore was possible. The use of relatively costly acetic anhydride in this reaction, however, made such a process economically less attractive than desired.

SUMMARY OF THE INVENTION

It has now been found that methyl benzenes may be oxidized with air or oxygen to form phenolic acetates and formaldehyde or methylene diacetate in the presence of acetic acid in place of acetic anhydride when reaction is carried out in the presence of a strong dehydrating agent, namely phosphorus pentoxide, a strong acid catalyst, and benzaldehyde.

As in copending application, Ser. No. 957,614, this reaction may be carried out at convenient rates and good yields under mild conditions of as low as 80° C. and oxygen pressures of 1 atmosphere.

The resulting acetates may then be converted to the respective phenolic compounds and formaldehyde or paraformaldehyde by pyrolysis or the like.

DESCRIPTION OF THE INVENTION

The process wherein acetic anhydride is employed may be depicted by the following equation, using toluene as an example:

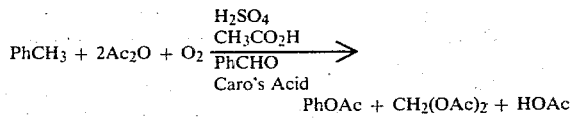

in which acetic acid is being used solely as a solvent, together with Caro's acid, a promoter for the reaction.

By contrast, the present invention may be represented by the following equation.

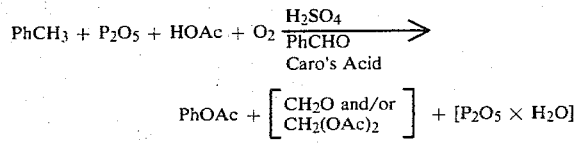

It will be understood, of course, that this method is equally applicable to other methyl benzenes such as xylenes and trimethyl benzenes, e.g., mesitylene and pseudocumene.

In general, the process is carried out by oxidizing the desired methyl benzene in acetic acid with air or oxygen in the presence of benzaldehyde, $P_2O_5$ and a strong acid catalyst in the liquid phase at pressures of at least 1 atmosphere and at temperatures as low as 80° C. to form equimolar amounts of a phenolic acetate and formaldehyde and/or methylene diacetate, together with lesser amounts of certain methylbenzene-derived by-products. The phenolic acetate and methylene diacetate, following separation, may then be pyrolyzed to form the corresponding phenolic compound and formaldehyde respectively.

As aforementioned, the reactants are methyl benzenes, such as toluene, xylene (ortho, meta, or para) and trimethyl benzenes such as mesitylene and pseudocumene, together with benzaldehyde and oxygen or air, in the presence of an acid catalyst, preferably $H_2SO_4$, and, as the novel feature of this invention, acetic acid and $P_2O_5$. The weight ratio of methyl benzene to acetic acid should desirably be in the range of from about 10:1 to 1:10 and preferably 5:1 to 1:2, while the weight ratio of $H_2SO_4$ to methyl benzene should generally be from about $5 \times 10^{-4}$ to $1 \times 10^{-2}$, and preferably $1 \times 10^{-3}$ to $5 \times 10^{-3}$.

The amount of benzaldehyde employed is about 0.01 to 1.0 moles, and preferably 0.05 to 0.10 moles, per mole of methyl benzene.

The amount of $P_2O_5$ employed is about 1:1 to 1:20 moles, and preferably 1:2 to 1:5 moles, per mole of acetic acid.

If desired, the reaction may be run in excess methyl benzene reactant as a solvent, or in a suitable organic solvent such as benzene or chlorobenzene.

It has further been found that persulfate promoters such as sodium persulfate, potassium persulfate, persulfuric acid or Dry Caro's acid are particularly effective promoters for this oxidation reaction. These promoters are desirably used in amounts of from about $10^{-3}$ to $10^{-1}$ gm per gram of methyl benzene.

The reaction, which employs oxygen or equivalent amounts of air, can, and should, as aforestated, be carried out under relatively mild conditions, i.e., at temperatures of at least 80° C., up to about 105° C., and most desirably at about 90°–120° C., and at air or $O_2$ pressures of at least 1 atmosphere, up to about 10 atmospheres, with the lower ranges of both pressure and temperatures being preferred.

The reaction product containing the phenolic acetate and methylene diacetate, as well as acetic acid, and lesser amounts of methyl benzene derived by-products, and the like is then routinely treated to remove the acid catalyst, following which the two acetate products may be separated by distillation under vacuum.

The recovered phenolic acetate is then converted to phenol, cresol or the like by pyrolysis. This is conventionally achieved by heating the acetate at temperatures of from about 500° C. to 1000° C., preferably at about 625° C., and preferably to the presence of a catalyst such as triethyl phosphate and recovering the desired product by routine means.

In a like manner, the pyrolysis of methylene diacetate yields formaldehyde and acetic anhydride. This pyrolysis is conventionally carried out in one step in a homogeneous gas phase reaction, at about 450°–550° C. under reduced pressure.

The following examples are provided solely for purposes of illustrating but not limiting the novel process of the invention.

EXAMPLE 1

Into a manometric gas-recirculating oxidation apparatus was charged, under nitrogen

| | |
|---|---|
| Toluene | 21.4 ml. |
| Acetic Acid | 12.0 ml. |
| Benzaldehyde | 1.0 ml. |
| Phosphorous Pentoxide | 2.5 g. |
| Dry Caro's Acid | 0.5 g. |

The reaction mixture was heated to 102°, nitrogen was replaced by pure oxygen and the gas recirculating pump was turned on, sparging oxygen below the surface of the liquid at a rate of 350 ml./min. The oxygen uptake was measured in the mercury filled buret by displacement. Liquid samples were withdrawn from the reaction flask, and analyzed by standard gas chromatographic techniques.

After 1 hr. and 15 min. 197 ml. of oxygen had been absorbed. The toluene oxidation products were analyzed by GC. The wt.% values given are normalized on the basis of the following compounds: Methylene diacetate (MDA), benzaldehyde (BAL), phenyl acetate (PA), benzyl acetate (BAC), phenyl hemiformal acetate (PHF), and other, unidentified products appearing within the same GC scanning range. Although benzaldehyde is an added reagent it is conveniently included in the product analysis since it appears within the GC scanning range of toluene oxidation products. The reaction mixture contained, calculated on the basis of the normalized product scans: (MDA) 8%, (BAL) 30%, (PA) 23%, (BAC) 5%, other unidentified products within the same scanning range 34%. The reaction was continued for 5 hrs. at the end of this period the reaction product analyzed: MDA 14%, BAL, 30%, PA 20%, BAC 3%, others 33%.

EXAMPLE 2

Into a 300-ml. rocking bomb was charged:

| | |
|---|---|
| Toluene | 43.0 ml. |
| Acetic Anhydride | 2.0 ml. |
| Acetic Acid | 16.0 ml. |
| Benzaldehyde | 2.0 ml. |
| Dry Caro's Acid | 1.0 g. |
| Phosphorus Pentoxide | 5.0 g. |
| Sulfuric Acid | 0.11 g. |

The bomb was pressurized with 120 psi of oxygen and 170 psi nitrogen and was heated to 120° C. over a 30 min. period, then held at 120° C. for 1 hr. 25 min. The pressure drop after cooling to room temperature was 32 psi. The reaction mixture was analyzed for the toluene oxidation products as in Example 1. MDA 21%, BAL 18%, PA 21%, BAC 5%, phenylhemiformal acetate (PHF) 8%, others 26%.

EXAMPLE 3

Into the manometric recirculating reactor was charged:

| | |
|---|---|
| Toluene | 21.4 ml. |
| Acetic Acid | 12.0 ml. |
| Benzaldehyde | 1.0 ml. |
| Dry Caro's Acid | 0.5 g. |
| Anh. Magnesium Sulfate | 3.0 g. |

The reaction was carried out as in Example 1 at 103° C. for 2 hrs. and 30 min. At the end of this period no detectable oxidation products were shown by the gas chromatography.

EXAMPLE 4

Pyrolysis of methylene diacetate to paraformaldehyde and acetic anhydride is accomplished thermally at about 500° C. in a known manner.

Alternatively, the catalytic pyrolysis of methylene diacetate is carried out at about 300° C. in the presence of a catalyst composed of 5% sodium chloride mixed with silica gel, dried and calcined. The methylene diacetate, dissolved in n-hexane, is passed through a passified tubular reactor packed with the catalyst at a space velocity of 900 hr$^{-1}$ and a temperature of 300° C. Paraformaldehyde and acetic anhydride condense downstream and are separated routinely. Selectivities exceed 93% for acetic anhydride and 95% for methylene diacetate.

EXAMPLE 5

Pyrolysis of phenyl acetate to phenol and ketene is accomplished thermally at 625° C. by passing it through a well-conditioned tubular reactor. The effluent is condensed to give 84% yield of phenol and 89% yield of ketene.

The reaction may be carried out at a somewhat lower temperature in the presence of triethyl phosphate catalyst at space velocities of between 900 and 1000 hr$^{-1}$. Yields in excess of 90% are obtained.

Cresyl acetate may be converted in a like manner to cresol.

What is claimed is:

1. A process for the oxidation of methyl benzenes to form phenolic acetates, and formaldehyde or methylene diacetate, or mixtures thereof, which comprises contacting said methyl benzenes with air or oxygen, and acetic acid and $P_2O_5$, in the presence of a strong acid catalyst and benzaldehyde at temperatures of at least about 80° C. and pressures of at least about 1 atmosphere, said benzaldehyde being present in amounts of from about 0.01–1.0 mole based on the methyl benzene.

2. The process of claim 1 wherein the acid catalyst is $H_2SO_4$.

3. The process of claim 1 wherein the temperature is from about 80° C. to 150° C.

4. The process of claim 1 wherein the pressure is from about 1 to 10 atmospheres.

5. The process of claim 1 wherein a suitable organic solvent is employed.

6. The process of claim 1 wherein the reaction is carried out in the presence of a persulfate promoter.

7. The process of claim 6 wherein the promoter is Dry Caro's Acid.

8. The process of claim 1 wherein the methyl benzene is toluene and the products are phenyl acetate and methylene diacetate.

9. The process of claim 1 wherein the methyl benzene is xylene and the products are cresyl acetate and methylene diacetate.

* * * * *